(12) United States Patent
Weber et al.

(10) Patent No.: US 11,684,350 B2
(45) Date of Patent: Jun. 27, 2023

(54) DEFLECTABLE LEAD DELIVERY CATHETER HAVING SLITTABLE PULL RING

(71) Applicant: Pacesetter, Inc., Sylmar, CA (US)

(72) Inventors: Adam Weber, Minnetonka, MN (US); Jennifer Heisei, Princeton, MN (US)

(73) Assignee: PACESETTER, INC., Sylmar, CA (US)

( * ) Notice: Subject to any disclaimer, the term of this patent is extended or adjusted under 35 U.S.C. 154(b) by 270 days.

(21) Appl. No.: 16/417,116

(22) Filed: May 20, 2019

(65) Prior Publication Data

US 2019/0357893 A1 Nov. 28, 2019

Related U.S. Application Data

(60) Provisional application No. 62/676,859, filed on May 25, 2018.

(51) Int. Cl.
| | |
|---|---|
| *A61B 17/00* | (2006.01) |
| *A61B 17/34* | (2006.01) |
| *A61N 1/362* | (2006.01) |
| *A61N 1/05* | (2006.01) |
| *A61M 25/01* | (2006.01) |

(52) U.S. Cl.
CPC .... *A61B 17/00234* (2013.01); *A61B 17/3468* (2013.01); *A61N 1/362* (2013.01); *A61B 2017/00309* (2013.01); *A61B 2017/00327* (2013.01); *A61M 25/0138* (2013.01); *A61N 1/056* (2013.01)

(58) Field of Classification Search
CPC .... A61B 2017/00309; A61B 2017/003; A61B 2017/00323; A61B 2017/00327; A61B 17/00234; A61B 17/3468; A61N 1/362
See application file for complete search history.

(56) References Cited

U.S. PATENT DOCUMENTS

| | | | |
|---|---|---|---|
| 6,517,477 B1* | 2/2003 | Wendlandt | A61B 1/00147 604/95.01 |
| 8,406,899 B2 | 3/2013 | Reddy et al. | |
| 9,610,438 B2 | 4/2017 | Schilling | |
| 9,861,787 B2 | 1/2018 | Tegg | |
| 9,919,132 B2 | 3/2018 | Tegg et al. | |
| 2010/0274270 A1* | 10/2010 | Patel | A61B 5/066 606/159 |
| 2013/0096587 A1* | 4/2013 | Smith | A61B 17/320758 606/159 |

(Continued)

*Primary Examiner* — Sarah A Simpson
*Assistant Examiner* — Raihan R Khandker
(74) *Attorney, Agent, or Firm* — Womble Bond Dickinson (US) LLP (57) ABSTRACT

A lead delivery catheter having a slittable pull ring is described. The lead delivery catheter includes a deflection wire attached to the slittable pull ring to deflect the catheter. The slittable pull ring has several ring holes arranged in a pattern. The pull ring is located distal to a tubular braid of the lead delivery catheter, and a size and pattern of the ring holes can be similar to a size and pattern of holes in the tubular braid. The structural similarity between the pull ring and the tubular braid facilitates use of a consistent cutting force to slit through the tubular braid and the pull ring of the lead delivery catheter. Other embodiments are also described and claimed.

18 Claims, 7 Drawing Sheets

(56) References Cited

U.S. PATENT DOCUMENTS

| | | | | |
|---|---|---|---|---|
| 2014/0309661 A1* | 10/2014 | Sheps | .................. | A61M 25/01 |
| | | | | 606/130 |
| 2018/0250150 A1* | 9/2018 | Majercak | ........... | A61B 17/3468 |
| 2020/0046387 A1* | 2/2020 | Kuniyasu | ............ | A61M 25/104 |

* cited by examiner

DEFLECTABLE LEAD DELIVERY CATHETER HAVING SLITTABLE PULL RING

This application claims the benefit of priority of U.S. Provisional Patent Application No. 62/676,859, filed May 25, 2018, entitled "Deflectable Lead Delivery Catheter Having Slittable Pull Ring," and that patent application is incorporated herein by reference in its entirety to provide continuity of disclosure.

BACKGROUND

Field

The present disclosure relates to catheter medical devices and related methods of using catheter medical devices. More specifically, the present disclosure relates to steerable catheters and methods for slitting steerable catheters.

Background Information

Artificial pacemakers provide an electrical stimulation to the heart to perform cardiac pacing when a conduction system of the heart fails to naturally provide synchronized atrial and ventricular contractions at healthy rates and intervals. The cardiac pacing provides relief from symptoms of the cardiac failure, and even life support, for many patients.

The current standard of care for pacing the human heart is to pace the ventricle by myocardial stimulation. While pacing the ventricular myocardium is commonly performed, the practice can have drawbacks. For example, myocardial stimulation can cause non-physiologic contraction that predisposes patients to accelerated development of heart failure.

To address the recognized drawbacks of myocardial stimulation, alternative pacing paradigms are contemplated. For example, the human ventricle can be paced by directly stimulating the specialized ventricular conduction system, e.g., the His/Purkinje system. Pacing the His/Purkinje system may completely ameliorate the deleterious effects of ventricular pacing. This pacing technique is limited in clinical practice, however, because the target tissue, e.g., the bundle of His, is small and difficult to access with available pacing tools. More particularly, it can be technically challenging to deliver a distal end of a conventional delivery catheter to the target tissue because conventional delivery catheters have fixed curves that are difficult to maneuver precisely within the patient anatomy.

A steerable catheter can facilitate access to the target tissue. The steerable catheter increases an ability of an operator to navigate a distal end of the catheter to a target site. For example, one or more sections of the steerable catheter can be deflected such that the steerable catheter has a variable curve. The variable curve can be adjusted by the operator to maneuver the distal end of the catheter more precisely within the patient anatomy, and to access the target site more easily. When the distal end is directed toward the target site, a pacing lead can be advanced through the distal end and affixed to the target tissue.

Steerable catheters commonly include components such as steering wires or rings incorporated in a body of the catheter. The steering components can be manipulated by the operator to selectively tension the catheter and deflect the catheter section(s). After affixing the lead to the target tissue, the steerable catheter is removed from the target anatomy. The steerable catheter is removed over the lead by slitting the catheter body (including the steering components) longitudinally such that the lead can pass through the slit to separate the lead and the steerable catheter.

SUMMARY

Steerable catheters can be advantageous over traditional pre-curved catheters for delivering pacing leads to the specialized ventricular conduction system. In addition to improved maneuverability, steerable catheters can decrease costs accrued by a catheterization lab in stocking a large number and variety of fixed curve catheters, which would otherwise be required to pinpoint the target site. Steerable catheters, however, do have some comparative drawbacks. Slitting a steerable lead delivery catheter during removal can be more difficult and/or be accompanied by more complications, as compared to slitting conventional pre-curved lead delivery catheters. For example, the cutting force required to advance a blade of a cutting device through a steerable lead delivery catheter may vary over the catheter length, since more force may be required to cut through portions of the catheter having the steering components as compared to portions of the catheter without the steering components. This variation in cutting force can be transmitted by the steering catheter to the pacing lead, and the pacing lead can be jolted or dislodged from the target tissue.

A lead delivery catheter that is steerable and includes a slittable pull ring is provided. In an embodiment, the lead delivery catheter includes a catheter shaft coupled to a handle. The catheter shaft has a pull ring near a distal end, and a deflection wire coupled to the pull ring. The deflection wire extends proximally from the pull ring to a proximal end of the catheter shaft. The handle can be mounted on the proximal end of the catheter shaft and coupled to the deflection wire to apply tension to the deflection wire. When the deflection wire is tensioned, the catheter shaft can deflect from a straight undeflected state to a curved deflected state. In the deflected state, the catheter shaft can be steered to a target anatomy. A pacing lead can then be advanced through the catheter shaft to the target anatomy. The pacing lead can remain within the target anatomy and the catheter shaft can be removed over the pacing lead. To remove the lead delivery catheter, a blade of a cutting tool can slit through the catheter shaft from the proximal end to the distal end. The slitting action is facilitated by a structure of the pull ring, which resists the blade with a reactive load that is similar to a reactive load applied to the blade by a tubular braid within the catheter shaft. More particularly, as the blade is advanced through the tubular braid and the slittable pull ring, minimal variation is seen in the cutting force required to advance the blade. The consistent reactive loads exerted by both the pull ring and the tubular braid can stem from a mesh region of the pull ring. The mesh region can have several holes that are sized and patterned similar to holes of the tubular braid, and thus, the ring and braid can be similarly structured. Since a consistent reactive load is applied to the blade by the ring and the braid, a likelihood that the catheter shaft will jolt the pacing lead during removal is reduced. Accordingly, the pacing lead may remain intact in the target anatomy.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in

DETAILED DESCRIPTION

Embodiments describe a delivery catheter having a slittable pull ring and methods for using the delivery catheter to deliver a medical device to a target anatomy. The delivery catheter can be used in a catheterization laboratory to deliver a pacing lead to a specialized ventricular conduction system, and thus, may be a lead delivery catheter. The delivery catheter, however, may be used in other applications, such as other diagnostic or therapeutic procedures, and thus, reference to the delivery catheter as being a lead delivery catheter is not limiting. Furthermore, the slittable pull ring, which is described below as being a steering component of the lead delivery catheter, may be incorporated into any catheter (steering or non-steering) that is slit during use.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a central axis of a lead delivery catheter. Similarly, "proximal" may indicate a second direction opposite to the first direction. Such terms are provided to establish relative frames of reference, however, and are not intended to limit the use or orientation of a lead delivery catheter to a specific configuration described in the various embodiments below.

In an aspect, a lead delivery catheter is provided. The lead delivery catheter is steerable to direct a pacing lead to a specific location in a target anatomy. Accordingly, a catheter shaft of the lead delivery catheter includes several steering components, e.g., a pull ring used to compress the catheter shaft during steering. The lead delivery catheter may be removable over the pacing lead by slitting a wall of the catheter shaft and pulling the catheter shaft away from the pacing lead while the lead is embedded in the target anatomy. Accordingly, the catheter shaft and the steering components, e.g., the pull ring, may be slit by a blade. The slittable pull ring may include a structure and size that allows the blade to cut through the entire length of the catheter shaft with a consistent cutting force. For example, the pull ring may include ring holes that match a size or pattern of braid holes in a tubular braid of the catheter shaft, and thus, an overall material density and distribution of the pull ring can be similar to that of the tubular braid. Accordingly, the cutting force required to cut through the slittable pull ring may be similar to the cutting force required to cut through the tubular braid.

Figure 1:
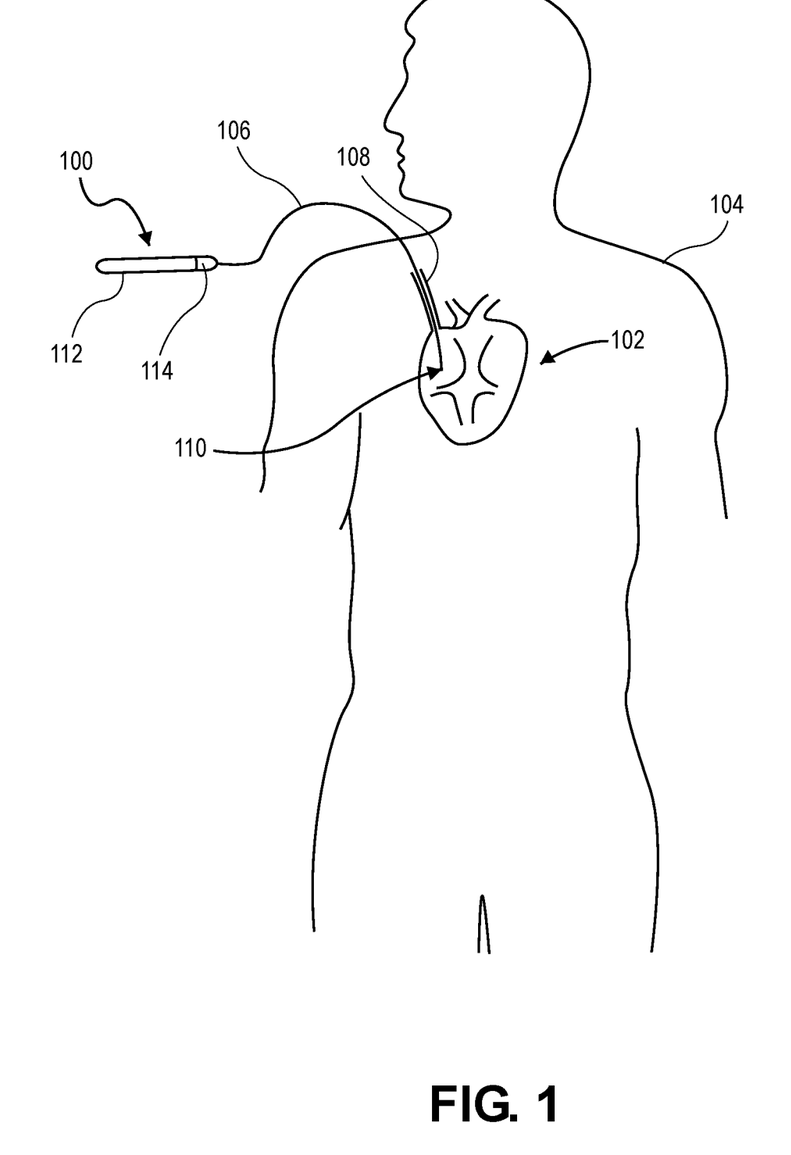
FIG. 1 is a pictorial view of a lead delivery catheter being steered to a target anatomy, in accordance with an embodiment.

Referring to FIG. 1, a pictorial view of a lead delivery catheter being steered to a target anatomy is shown in accordance with an embodiment. A lead delivery catheter 100 can be used to perform a medical procedure on a target anatomy, such as a heart 102 of a patient 104. A catheter shaft 106 of the lead delivery catheter 100 can be advanced to the target anatomy of the patient 104 intravascularly through a body lumen 108, e.g., via a subclavian access route, or via other routes. FIG. 1 illustrates advancement of the catheter shaft 106 along a femoral route, however, it will be appreciated that other approaches may be used and the illustrated approach is not limiting. The approach may be selected according to a length of a lead of an implantable pacemaker/defibrillator and/or a target placement of the implantable pacemaker/defibrillator. For example, when the implantable pacemaker is intended to be placed in a pocket in a chest, or near a shoulder, of the patient 104, the catheter shaft 106 can be advanced to the target anatomy along a subclavian approach. The target anatomy can include a chamber of the heart 102, within which a medical procedure, such as ablation, mapping, or pacing, is to be performed.

Figure 4A:
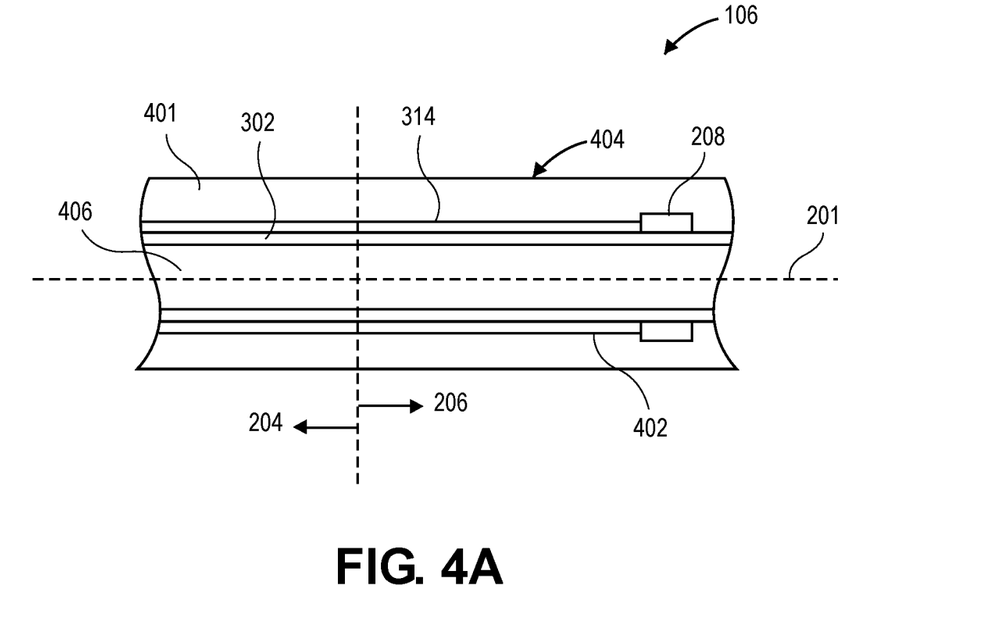
FIGS. 4A-4B are sectional views of a lead delivery catheter in different deflection states, in accordance with an embodiment.
Figure 4B:
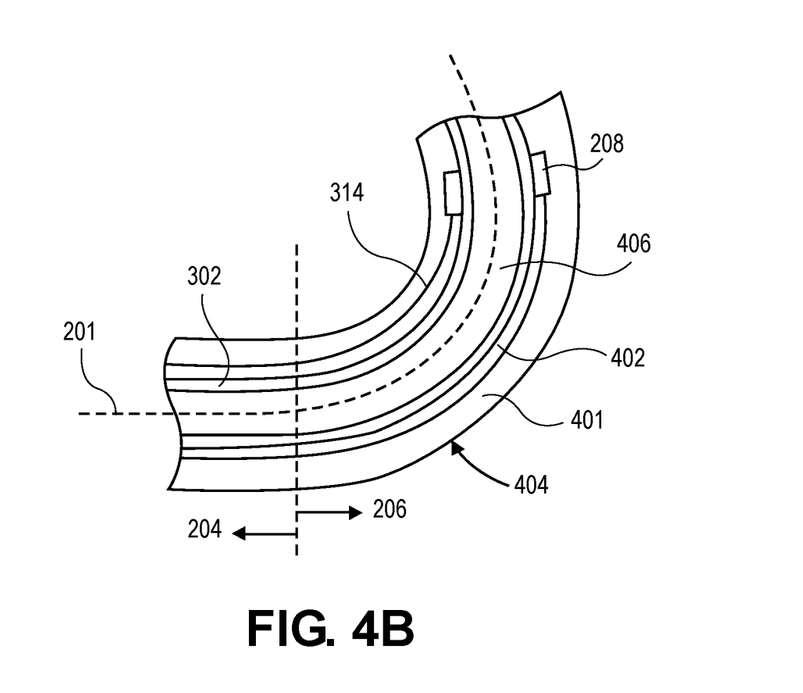

The lead delivery catheter 100 includes the catheter shaft 106 having a distal end 110 that is steered to the target anatomy, and a handle 112 coupled to a proximal end of the catheter shaft 106. The handle 112 can be manipulated to control a curvature of the catheter shaft 106. For example, the handle 112 may include an adjustment feature 114, such as a knob, lever, switch, etc., which interacts with a steering component of the catheter shaft 106 to deflect the catheter shaft. By way of example, rotation of a knob can apply tension to a deflection wire of the catheter shaft 106, and the tension applies a localized compression to the catheter shaft 106 to result in a deflection of the distal end 110 of the catheter shaft 106 (FIGS. 4A-4B). The distal end 110 of the deflected shaft can be directed to a target site, which may be a region of tissue that is several millimeters wide. For example, the target site can be the His bundle located near the apex of the triangle of Koch in the right atrium of the heart 102. The target site can be at any location targeted by the physician, and thus, examples of specific target sites such as the His bundle are provided by way of example, and are not necessarily limiting. A pacing lead (not shown) can be delivered through the steered catheter shaft 106 to engage the target site.

Figure 2:
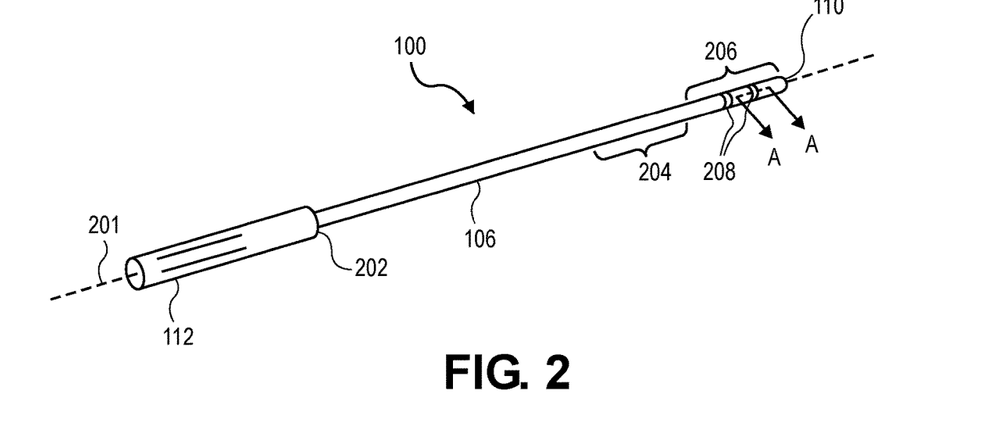
FIG. 2 is a perspective view of a lead delivery catheter having a slittable pull ring, in accordance with an embodiment.

Referring to FIG. 2, a perspective view of a lead delivery catheter having a slittable pull ring is shown in accordance with an embodiment. The lead delivery catheter 100 includes a catheter shaft 106, which extends along a central axis 201 from a proximal end 202 to the distal end 110. A non-deflectable segment 204 can extend along the central axis 201 between the proximal end 202 and a deflectable segment 206. For example, the non-deflectable segment 204 can extend from the proximal end 202 to the deflectable segment 206.

In an embodiment, the deflectable segment 206 includes one or more pull rings 208 incorporated in the catheter shaft 106. For example, the pull ring(s) 208 may be embedded in the catheter shaft 106, attached to an inner or outer surface of the catheter shaft 106, or otherwise mounted on a component of the catheter shaft 106. The pull ring 208 may be coupled to the handle 112, such that actuation of the adjustment feature 114 causes relative movement between the pull ring 208 and the proximal end 202 of the catheter shaft 106. The relative movement steers the distal end 110 of the catheter shaft 106, as described below.

Figure 3:
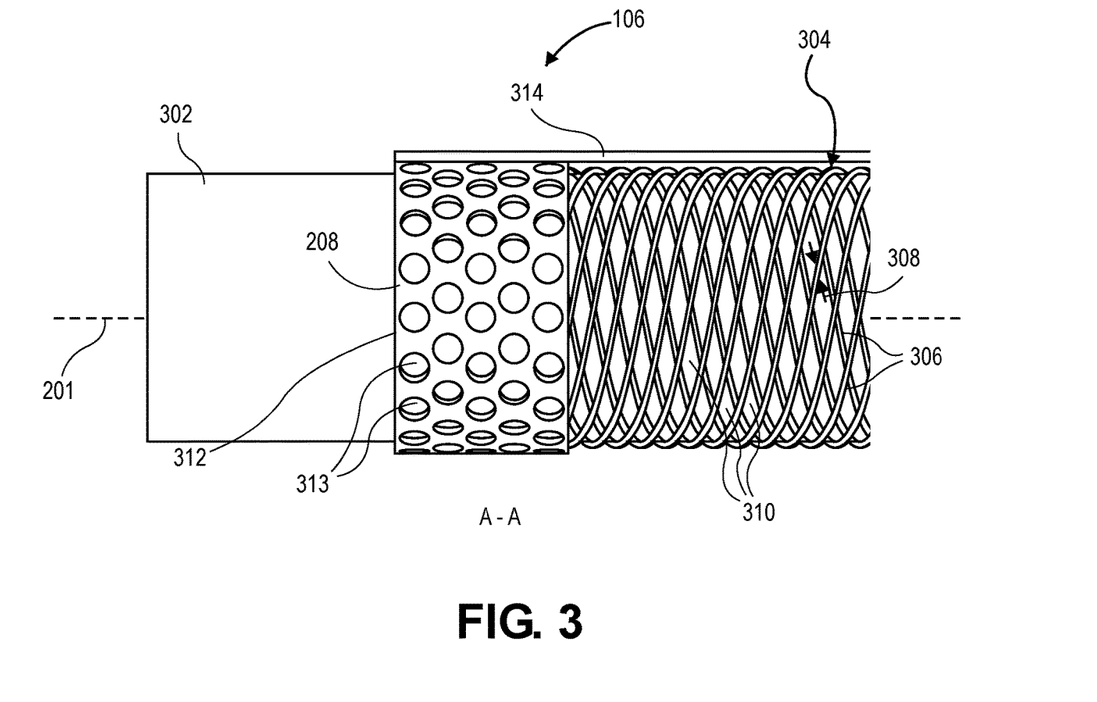
FIG. 3 is a sectional view of a deflectable segment of a lead delivery catheter, taken about line A-A of FIG. 2, in accordance with an embodiment.

Referring to FIG. 3, a sectional view of a deflectable segment of a lead delivery catheter, taken about line A-A of FIG. 2, is shown in accordance with an embodiment. The catheter shaft 106 can include several tubular components. In an embodiment, the catheter shaft 106 includes a tubular liner 302 extending along the central axis 201. The tubular liner 302 may be an inner member having a lumen to deliver the pacing lead into the patient 104, and accordingly, the tubular liner 302 may be formed from materials having suitable strength and friction characteristics. By way of example, the tubular liner 302 can be an extruded polytetrafluoroethylene (PTFE) tube sized to receive the pacing lead. Such material examples throughout this description are not to be considered limiting, however, and the tubular liner 302 may be formed from other materials, including polyether block amides, nylon, thermoplastic elastomers, etc.

In an embodiment, the catheter shaft 106 includes a tubular braid 304 extending along the central axis 201 over the tubular liner 302. The tubular braid 304 can reinforce the catheter shaft 106 over a length within one or more of the non-deflectable segment 204 or the deflectable segment 206. More particularly, the tubular braid 304 can provide stiffness to the catheter shaft 106, which increases a columnar strength of the catheter shaft 106, transmits torque along the length of the catheter shaft 106, or imparts a resilience to the catheter shaft 106 that can bias the catheter shaft 106 toward an undeflected state, e.g., a straightened configuration.

The tubular braid 304 can include several strands 306 interlaced around the central axis 201 in a braid structure. The braid structure can have a braid pattern and density defined by a number of strands 306 and picks per inch (PPI), as is known in the art. There is a wide variety of possibilities for the PPI and number of strands 306 in the braid pattern. By way of example only, the tubular braid 304 can include a uniform braid structure. For example, the tubular braid 304 can have 16 wires at about 45 to about 60 PPI. Alternatively, the tubular braid 304 can include a variable braid structure. For example, the tubular braid 304 can have 16 wires at about 10 PPI in the deflectable segment 206 of the catheter shaft 106 and 50 PPI in the non-deflectable segment 204 of the catheter shaft 106. Again, these examples are for illustrative purposes and are not limiting.

Each strand 306 of the tubular braid 304 can include a wire having a uniform cross-sectional area, e.g., round, oval, or rectangular, over a wire length. The strands 306 can be formed from various materials, e.g., stainless steel, shape memory alloy, or polymer materials. Furthermore, a size of the cross-sectional area, such as a height or width of the cross-sectional area, can be in a range of about 0.002 to 0.020 inch. For example, the area height, which may be referred to as a strand thickness 308, may be about 0.004 inch. The strands 306 can be interlaced around braid holes 310 along the catheter shaft 106. For example, the braided wires can form diamond-shaped braid holes 310 around the central axis 201. Each braid hole 310 can have a hole dimension, e.g., a hole width in a circumferential direction or a hole length in a direction of the central axis 201. The hole dimension may depend on a PPI of the braid structure.

In an embodiment, a pull ring 208 is mounted on the tubular liner 302. The pull ring 208 can have an annular or semi-annular (e.g., C-shaped) wall, which extends in a circumferential direction around the central axis 201. For example, an annular wall 312 of the pull ring 208 may surround the central axis 201. In the case of a semi-annular wall, the pull ring 208 may partially surround the central axis 201. For example, a C-shaped wall can have an axial slot that forms a discontinuity in the ring, and the ring can extend circumferentially from a first lateral edge on a first side of the slot to a second lateral edge on a second side of the slot over an angle of at least 180 degrees, e.g., between 270 to 330 degrees. As described further below, the pull ring 208 can include one or more ring holes 313 extending through a wall of the pull ring 208.

The catheter shaft 106 may include a deflection wire 314 extending along the tubular liner 302. The deflection wire 314 can extend in a direction of the central axis 201 between the proximal end 202 of the catheter shaft 106 and the pull ring 208. In an embodiment, the deflection wire 314 is axially arranged, e.g., the deflection wire 314 extends parallel to the central axis 201 over an entire length. Alternatively, the deflection wire 314 may have an axial and a circumferential component. For example, the deflection wire 314 may spiral around the tubular liner 302 from the proximal end 202 to pull ring 208.

The deflection wire 314 can be coupled to the pull ring 208 at an attachment point. For example, the deflection wire 314 can be attached to the deflection ring by a weld, an adhesive bond, or another connection. In an embodiment, the deflection wire 314 and the pull ring 208 are formed from similar materials, e.g., both from stainless steel or a shape memory alloy, and the deflection wire 314 is laser welded to the pull ring 208. In another embodiment, the deflection wire 314 and the pull ring 208 are formed from dissimilar materials, e.g., one from a stainless steel and another from a polymer or a shape memory alloy, and the connection between the components is formed by an adhesive bond.

Referring to FIG. 4A, a sectional view of a lead delivery catheter in an undeflected state is shown in accordance with an embodiment. In an undeflected state, the central axis 201 of the catheter shaft 106 can extend in a generally straight axial direction. The pull ring 208 can be laminated or otherwise encapsulated between the tubular liner 302 and a surrounding tubular component. For example, an external tubular component 401 can extend along the central axis 201 around the pull ring 208, the tubular liner 302, and the deflection wire 314. The catheter shaft 106 may optionally include a second deflection wire 402 to apply a load to the pull ring 208 in a direction opposite to the deflection wire 314. During manufacturing of the catheter shaft 106, the external tubular component and/or the tubular liner 302 can be heated to reflow polymer around the pull ring 208 and the tubular braid 304. The reflowed polymer holds the catheter shaft 106 components together in a laminated combination. The laminated combination can form a substantially unitary catheter shaft wall 404.

In an embodiment, the pull ring 208 remains fixed relative to the catheter shaft wall 404, however, the deflection wire 314 may be pushed and pulled relative to the catheter shaft wall 404. For example, the deflection wire 314 may extend through a lumen formed in the catheter shaft wall 404 such that actuation of the handle 112 can apply tension to the deflection wire 314. The tension may be transmitted through the deflection wire 314 to the pull ring 208. Accordingly, when the handle 112 pulls on the deflection wire 314, the pull ring 208 can apply a compressive load to the catheter shaft wall 404.

Referring to FIG. 4B, a sectional view of a lead delivery catheter in a deflected state is shown in accordance with an embodiment. The compressive load applied to the catheter shaft wall 404 by the pull ring 208 can generate a non-uniform stress distribution in the wall, which is accompanied by a strain variation that deflects the catheter shaft 106 along a transverse plane. More particularly, in the deflected state, the central axis 201 of the catheter shaft 106 can extend in a generally curved direction along the transverse plane. The curved catheter shaft 106 can be rotated as needed to steer and direct the distal end 110 of the catheter shaft 106 toward the target site. Accordingly, a pacing lead can be inserted into a lumen 406 of the catheter shaft 106 and advanced through the lead delivery catheter 100 to the target site.

Figure 5:
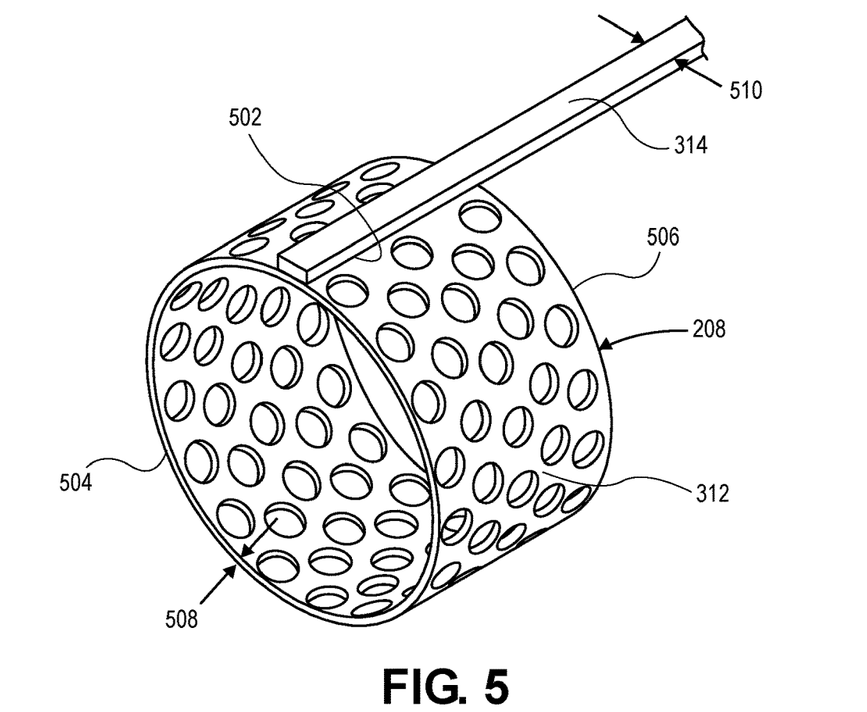
FIG. 5 is a perspective view of a steering component subassembly having a deflection wire attached to a slittable pull ring, in accordance with an embodiment.

Referring to FIG. 5, a perspective view of a steering component subassembly having a deflection wire attached to a slittable pull ring is shown in accordance with an embodiment. Steering of the lead delivery catheter 100 is facilitated by varying a curvature of the catheter shaft 106 as needed to direct the distal end 110 of the shaft in a desired direction. The curvature of the catheter shaft 106 may correspond to a magnitude of a tensile load applied to the deflection wire 314. For example, as more tension is applied to the deflection wire 314, the deflectable segment 206 of the catheter shaft 106 may curve more. Accordingly, a bond 502 between the pull ring 208 and the deflection wire 314 can be formed to withstand the applied tensile force. In an embodiment, the deflection wire 314 overlaps an outer surface of the pull ring 208, and the wire is bonded to the outer surface over an entire length of the overlap. The overlap length can equal an overall length of the pull ring 208. For example, a distal end of the deflection wire 314 may coincide with a distal edge 504 of the pull ring 208, and the bond 502 may extend proximally from the distal edge 504 to the proximal edge 506. In an embodiment, the length of the pull ring 208 and the bond 502 is between 0.030 inch and 0.150 inch, e.g., 0.070 inch. The pull ring length can be reduced, however, in proportion to an increase in a bond strength between the ring and the wire.

After the lead delivery catheter 100 has been steered to the target site and the pacing lead has been advanced through the catheter lumen 406 and engaged with the target tissue, the lead delivery catheter 100 is typically removed from the patient 104. Doing so allows a proximal end of the pacing lead to be connected to a pacemaker. For example, the pacemaker can be placed on a shoulder of the patient 104 to deliver an electrical stimulus through the pacing lead to the target tissue. The electrical connector that plugs into the pacemaker may have an outer dimension that is greater than a size of the lumen 406 of the catheter shaft 106. Accordingly, a cutting device is used to cut through the catheter shaft wall 404 from the proximal end 202 to the distal end 110 of the catheter shaft 106. The slit catheter shaft 106 can then be removed laterally from the pacing lead. As a blade of the cutting device is advanced, it cuts through the tubular braid 304 and the pull ring 208. It will be appreciated that the pull ring 208 and the tubular braid 304 may have different cutting characteristics. More particularly, differences in materials and structures of the pull ring and the braid structures may require different cutting forces to be applied to advance the blade through the components. In an embodiment, the pull ring 208 of the lead delivery catheter 100 is a slittable pull ring 208 that minimizes differences in the cutting characteristics between the ring and the braid. Accordingly, the physician can advance the blade through the catheter shaft wall 404 with a substantially uniform cutting force that reduces a likelihood of jolting or dislodging the pacing lead from the target tissue.

In an embodiment, the pull ring 208 is located to facilitate slitting of the catheter shaft wall 404. The pull ring 208 can be located along the catheter shaft 106 at a position that will minimize a change in cutting force as the blade is moved distally relative to the catheter shaft 106. In an embodiment, the pull ring 208 is located distal to the tubular braid 304 (FIG. 3). More particularly, the distal edge 504 of the pull ring 208 can be distal to a distal end of the tubular braid 304. Similarly, the proximal edge 506 of the pull ring 208 may be distal to the distal end of the tubular braid 304. The proximal edge 506 of the pull ring 208 may be located near the distal end of the tubular braid 304, e.g., within 1-5 millimeters of the distal end of the tubular braid 304, such that a cutting blade moving distally through the tubular braid 304 will engage the proximal edge 506 of the pull ring 208 immediately after passing the distal end of the tubular braid 304. Accordingly, the braid will not jump between the components and the blade will see a nearly constant reaction force from the catheter shaft 106 while traversing the braid and ring in the axial direction. Furthermore, since the proximal edge 506 of the pull ring 208 is distal to the distal end of the tubular braid 304, the ring does not overlap the braid and the blade of the cutting tool does not have to slice through both the ring and the braid thicknesses at a same time.

In an embodiment, the pull ring 208 has a structure that facilitates slitting of the catheter shaft 106 during removal from the patient 104. For example, the pull ring 208 may be sized to have a wall thickness 508 that is similar to an overall thickness of the tubular braid 304. In an embodiment, the wall thickness 508 of the pull ring 208 is less than or equal to the strand thickness 308 of the tubular braid 304. For example, the strand thickness 308 of each strand 306 of the tubular braid 304 may be 0.004 inch, and accordingly, the wall thickness 508 of the pull ring 208 may be the same or less than the strand thickness 308, e.g., 0.003 inch.

Figure 6:
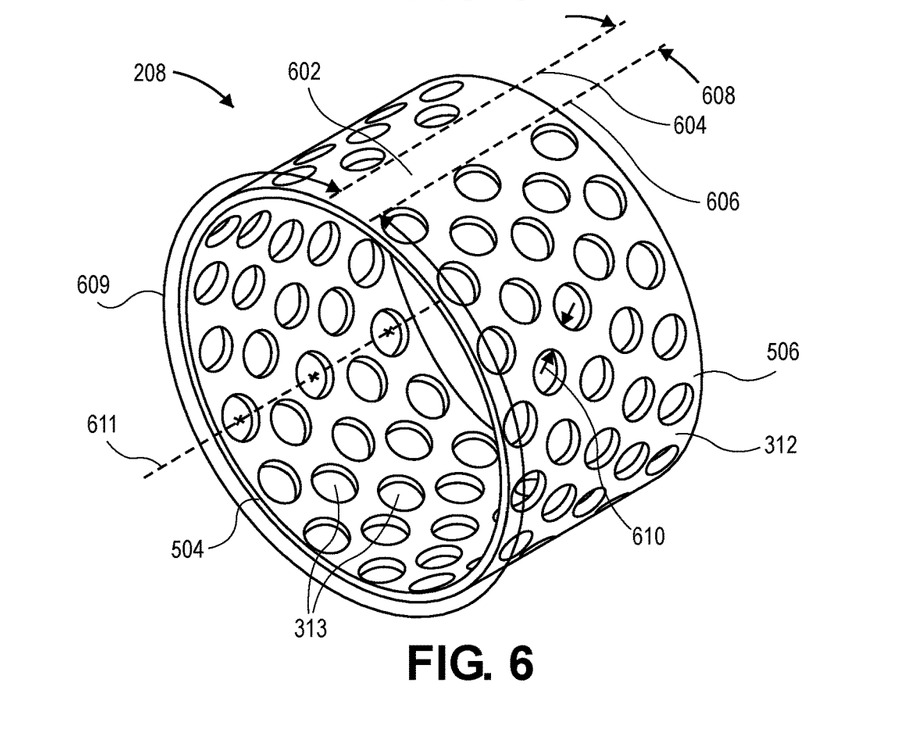
FIGS. 6-8 are perspective views of slittable pull rings, in accordance with various embodiments.

Referring to FIG. 6, a perspective view of a slittable pull ring having ring holes shaped differently than the braid holes is shown in accordance with an embodiment. The slittable pull ring 208 can include a reduced effective length in areas within which the blade of the cutting device is advanced. The effective length is a length of a solid portion of the ring wall between the proximal edge 506 and the distal edge 504 at any point along a circumference of the pull ring 208. By way of example, the pull ring 208 can include a solid region 602 circumferentially between a first lateral boundary 604 and a second lateral boundary 606. The solid region 602 can have a circumferential width 608 between the lateral boundaries, and a length that is equal to the length of the annular wall 312. More particularly, the solid region 602 can be a slice of the annular wall 312 that has the circumferential width 608 and is completely solid. Since the solid region 602 is completely solid, the effective length of the solid region 602 is equal to the length of the annular wall 312. By contrast, the slittable pull ring 208 can include a mesh region 609 on an opposite side of the first lateral boundary 604 from the solid region 602. For example, the mesh region 609 can extend circumferentially between the first lateral boundary 604 and the second lateral boundary 606 over an angle outside of the angle circumscribed by the solid region 602. The mesh region 609 can include several ring holes 313 that reduce a total amount of material of the pull ring 208 in the axial direction. By way of example, the mesh region 609 can have three or more ring holes 313 arranged around the central axis 201 in a pattern. As shown in FIG. 6, one or more of the ring holes 313 can be arranged along a reference axis 611. It will be appreciated that a length of the solid annular wall 312 along the reference axis 611 is less than a length between the distal edge 504 and the proximal edge 506. For example, when a single ring hole 313 is positioned along the reference axis 611, the effective length of the annular wall 312 along the reference axis 611 will be a distance between the distal edge 504 and the proximal edge 506 reduced by a diameter of the ring hole 313. Similarly, when three ring holes 313 are positioned along the reference axis 611 (FIG. 6) the effective length of the annular wall 312 along the reference axis 611 will be a distance between the distal edge 504 and the proximal edge 506 reduced by a sum of the diameters of the three ring holes 313. Accordingly, an effective length of the annular wall 312 at circumferential locations within the mesh region 609 may be less than the effective length of the solid region 602. A ratio of the effective length of the ring to the total length of the ring can be between 0.2 and 0.8 at any circumferential location in the mesh region 609. Accordingly, the mesh region 609 can have a porosity between 0.2 and 0.8, e.g., 0.5.

In an embodiment, the deflection wire 314 is attached to the solid region 602 (FIG. 5). The solid region 602 can be sized to receive the deflection wire 314. For example, the deflection wire 314 can have a wire width 510, and a circumferential width 608 of the solid region 602 may be greater than the wire width 510. Accordingly, the bond 502 between the deflection wire 314 and the annular wall 312 may extend over an entire length and width of a face of the deflection wire 314 that faces the annular wall 312.

The lead delivery catheter 100 may have bidirectional steering capability, and thus, the catheter shaft 106 can include a second deflection wire 402 (FIG. 4B). The second deflection wire 402 can extend along the tubular liner 302 on an opposite side of the shaft lumen 406 from the deflection wire 314. Similarly, the second deflection wire 402 can attach to the pull ring 208 at a location that is diametrically opposed to the bond 502 between the deflection wire 314 and the pull ring 208. Accordingly, the pull ring 208 can include a second solid region 602 (not shown) that is diametrically opposed to the solid region 602. The second solid region 602 can have characteristics similar to those described with respect to the solid region 602 above. For example, the second solid region 602 can be sized to receive the second deflection wire 402 and provide an attachment between the second deflection wire 402 and the annular wall 312 over an entire length of the pull ring 208. It will be appreciated that the catheter shaft 106 can be steered in a first direction by actuating the handle 112 to pull on the deflection wire 314, and the catheter shaft 106 can be steered in a second direction opposite to the first direction by actuating the handle 112 to pull on the second deflection wire 402.

In an embodiment, the circumferential width 608 of each solid region 602 of the pull ring 208 is minimized. By way of example, the circumferential width 608 may be less than twice the wire width 510 of the corresponding deflection wire 314. Accordingly, the circumferential width 608 of the mesh region 609 may be maximized such that the blade of the cutting device can more easily slice through the pull ring 208 at all locations except for the location where the deflection wire 314 is bonded to the annular wall 312. The blade of the cutting tool may be unable to easily slice through a solid band, and thus, the mesh region 609 facilitates slitting of the pull ring 208.

An overall structure of the pull ring 208, and more particularly, of the mesh region 609 of the pull ring 208, can be similar to an overall structure of the tubular braid 304 to reduce a difference in cutting force required to slit the catheter shaft wall 404 during catheter removal. The overall structure of the pull ring 208 may be defined in part by a pattern of the ring holes 313, and the overall structure of the tubular braid 304 may be defined in part by a pattern of the braid holes 310. The pattern of the ring holes 313 may be similar to the pattern of the braid holes 310. For example, the braid holes 310 may be arranged in the same pattern as the ring holes 313. The pattern similarity may result in the pull ring 208 and the tubular braid 304 having a same porosity, or respective porosities that are within +/−20% of each other. By way of example, a center-to-center distance between circumferentially adjacent braid holes 310 of the tubular braid 304 may be approximately equal to a center-to-center distance between circumferentially adjacent ring holes 313 of the pull ring 208. Similarly, a center-to-center distance between axially adjacent braid holes 310 of the tubular braid 304 may be approximately equal to a center-to-center distance between axially adjacent ring holes 313 of the pull ring 208.

Although the positioning of hole centers may be similar in the patterns of the mesh region 609 and the tubular braid 304, the ring holes 313 and the braid holes 310 may be differently sized or shaped. For example, the ring holes 313 may be circular and the braid holes 310 may be diamond-shaped. Accordingly, the ring holes 313 may have a hole diameter, and the braid holes 310 may have a hole length in an axial direction and a hole width in a circumferential direction. The hole diameter may be greater than the hole length and less than the hole width. In an embodiment, the spacing and sizing of the ring holes 313 is controlled to make the solid portion of the annular wall 312 similar in volume to the volume of strands 306 in the tubular braid 304. For example, an edge-to-edge distance 610 between ring holes 313 may be approximately the same as the strand thickness 308. The edge-to-edge distance 610 can be measured by drawing a line from a center of a first ring hole 313 to a center of an adjacent ring hole 313 and then measuring the distance along the line that traverses a solid portion of the annular wall 312. In an embodiment, adjacent ring holes 313 in the mesh region 609 are separated from each other by an edge-to-edge distance 610 less than twice the strand thickness 308. Accordingly, the distance between ring holes 313 can reasonably match the distance between braid holes 310 of the tubular braid 304. The similarity in material density between the pull ring 208 and the braid wire reduces a likelihood that the blade of the slitting tool will jolt or dislodge the pacing lead as the catheter is removed from patient 104.

In an embodiment, the ring hole pattern is a uniform pattern. For example, the ring holes 313 can be arranged in a lattice having repeating columns of holes offset from each other in a circumferential and axial direction. By way of example, a first column of three holes can be arranged along the reference axis 611. A second column of two holes can be arranged along another axis extending parallel to the central axis 201, which is circumferentially offset from the reference axis 611. Similarly, the holes in the second column can be axially shifted relative to the holes in the first column. A third column of three holes can be arranged along another axis extending parallel to the central axis 201, which is circumferentially offset from the first column and the second column. The second column can be circumferentially between the first column and the third column. The third column of holes may be axially aligned with the first column of holes. That is, holes of the first column and the third column can be spaced apart from the edges of the pull ring 208 by a same distance, as shown in FIG. 6. Also as shown in FIG. 6, there may be fewer, e.g., 2, holes in the second column as compared to the number of holes, e.g., 3, in the first and third columns.

In an embodiment, the ring hole pattern is a variable pattern. The ring holes 313 may be randomly distributed across the annular wall 312. Furthermore, a size of the ring holes 313 may vary such that the ring hole pattern is essentially amorphous or random. Nonetheless, the non-uniform ring holes 313 can be distributed in such a way that an edge-to-edge distance 610 between adjacent ring holes 313 is similar to the strand thickness 308. Whether the ring hole 313 pattern is a uniform pattern or a variable pattern, the material of the pull ring 208 can have an average density that is consistent across the pull ring 208 length at many of the locations in the circumferential direction (except for the solid region 602). Accordingly, the blade of the cutting tool can engage the mesh region 609 at nearly any circumferential location and experience a similar resistance to slitting, e.g., the physician can use a similar cutting force to advance a blade through the pull ring 208 at any circumferential location.

Figure 7:
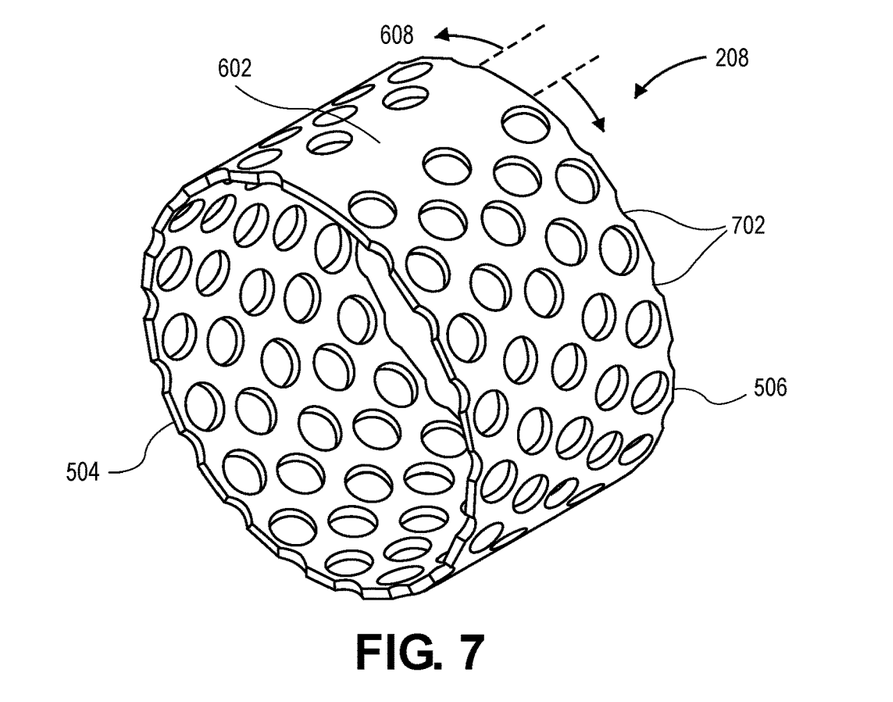

Referring to FIG. 7, a perspective view of a slittable pull ring having end notches is shown in accordance with an embodiment. The pull ring 208 can have features that facilitate engagement between the blade and the mesh region 609. Such engagement features may include notches 702 that direct the blade into the mesh region 609, and not the solid region 602. In an embodiment, the pull ring 208 can include a notch 702 in the proximal edge 506. The notch 702 may be a partial circle having an inward slope. Accordingly, when the blade engages the notch 702, it will be directed toward a bottom of the notch 702 before advancing distally into the mesh region 609. Furthermore, the notch 702 can reduce an amount of material that the blade is required to travel through when cutting the annular wall 312, and thus, the notch 702 can ease the slitting process. The notch 702 may have a variety of shapes. For example, rather than being a partial circle, the notch 702 may have a V-shape, or another shape that directs the blade of the cutting tool.

Figure 8:
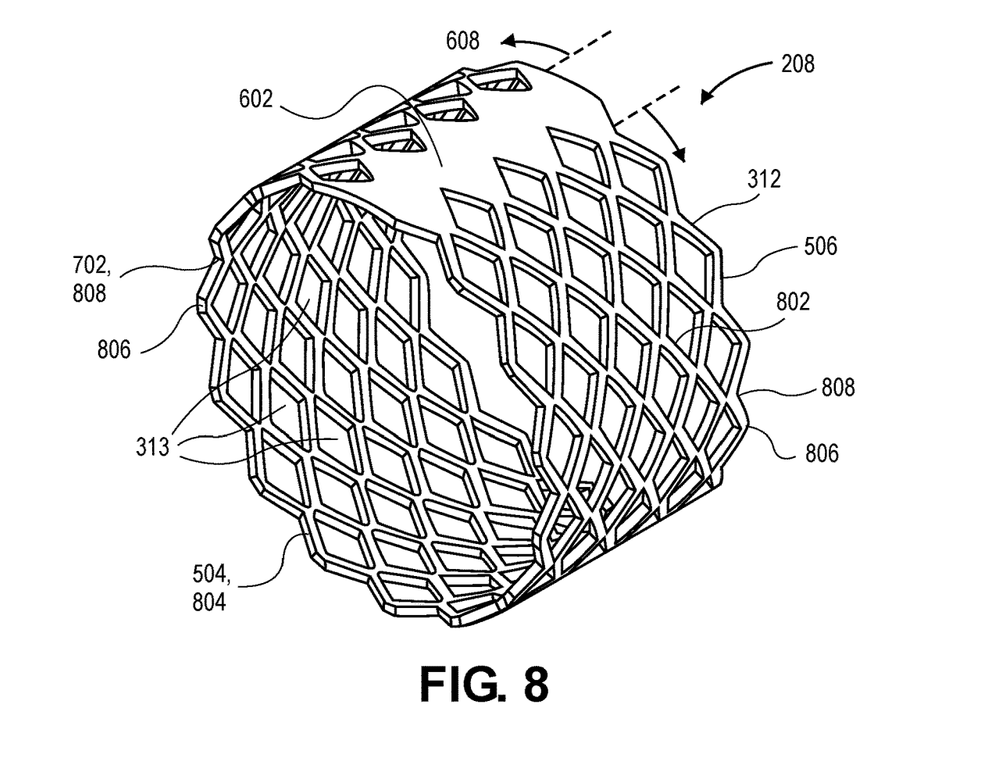

Referring to FIG. 8, a perspective view of a slittable pull ring having ring holes shaped similarly to the braid holes is shown in accordance with an embodiment. In an embodiment, the ring holes 313 are patterned and shaped similar to the braid holes 310. For example, the ring holes 313 can be formed as diamond-shaped cutouts in the annular wall 312. The ring hole cutouts can have hole widths and hole lengths that are similar to those of the tubular braid 304. Similarly, an interhole wall portion 802 between the ring holes 313 can have a similar dimension to the strands 306 of the tubular braid 304. The similarly sized and patterned holes can provide a pull ring 208 having a porosity in the mesh region 609 that is the same, or within +/−20%, of a porosity of the tubular braid 304. Accordingly, the blade will see similar resistance to cutting from both the pull ring 208 and the tubular braid 304, and the physician will not perceive a difference in cutting force as the blade advances through the catheter shaft 106.

The pull ring 208 can be fabricated using several techniques. For example, the illustrated pull rings 208 can be formed from a solid hypotube by cutting several holes into the wall of the hypotube. After the ring holes 313 are formed, circumferential cuts may be introduced to cut the hypo tube into several pull rings 208 having defined lengths. In an embodiment, a braiding technique may be used to form the pull ring 208. For example, several wires may be braided to form the pull ring 208 having the ring hole pattern and interhole wall portions 802 shown in FIG. 8. The braiding process can allow the structure of the pull ring 208 to be nearly identical to the structure of the tubular braid 304. To increase a columnar strength of the pull ring 208, the wires can be laser welded at intersection points such that the wires of the braided pull ring are effectively contiguous and joined at the intersection points. Other manufacturing processes may be used to form the pull ring 208 in accordance with the description provided herein.

Still referring to FIG. 8, in an embodiment, both ends (a proximal end 202 and a distal end 110) of the pull ring 208 are open. More particularly, the distal edge 504 and/or the proximal edge 506 of the pull ring 208 can follow a path that is not entirely within a plane that is transverse to the central axis 201. In an embodiment, the distal edge 504 and the proximal edge 506 follow a contour of the adjacent ring holes 313, and thus, the edges undulate axially forward and backward from respective edge peaks 806 to respective edge valleys 808. The open ends provide V-shaped notches 702 defined by the peaks and valleys. In the case of the distal edge 504, each edge peak 806 can be a distal maximum of the edge, and each edge valley 808 can be a proximal maximum of the edge. The distal maxima may be distal to the proximal maxima. Conversely, in the case of the proximal edge 506, each edge peak 806 can be a proximal maximum of the edge, and each edge valley 808 can be a distal maximum of the edge. The proximal maxima may be proximal to the distal maxima.

Figure 9:
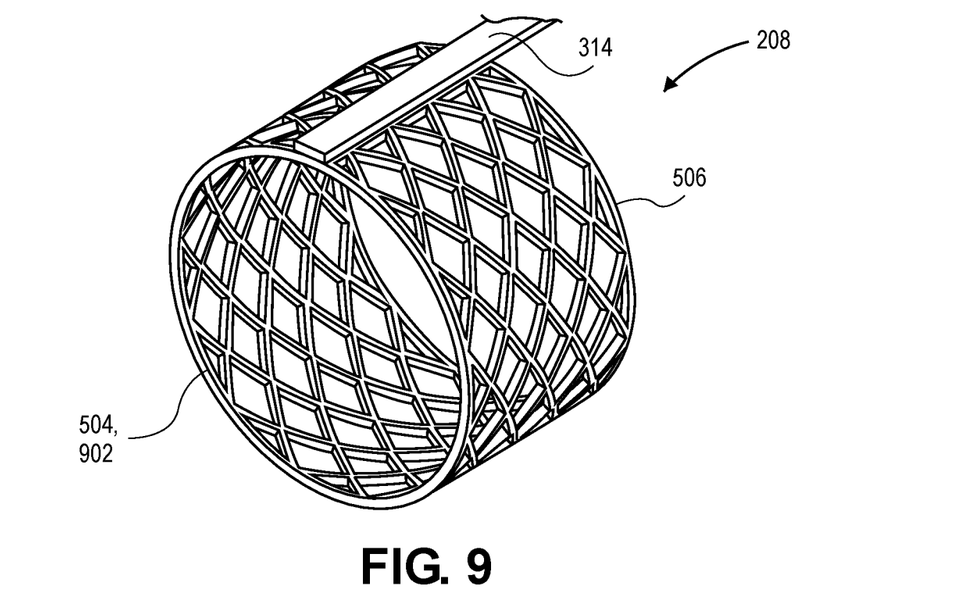
FIGS. 9-10 are perspective views of a steering component subassembly having a deflection wire attached to a slittable pull ring, in accordance with an embodiment.

Referring to FIG. 9, a perspective view of a slittable pull ring having closed ends is shown in accordance with an embodiment. The closed ends 902, in contrast to the open end 804 of FIG. 8, can have an edge that follows a path that is entirely within the plane that is transverse to the central axis 201. For example, the transverse plane can be orthogonal to the central axis 201, and the distal edge 504 and/or the proximal edge 506 can be circular edges that extend along the orthogonal plane around the central axis 201. In another embodiment (not shown), the transverse plane is not orthogonal to the central axis 201, and the edge(s) are elliptical edges extending along the transverse plane around the central axis 201. In any cases, the distal edge 504 and/or proximal edge 506 of the closed end(s) 902 of the pull ring 208 can be continuous such that a blade engaging the distal edge 504 will begin to slice through the pull ring 208 at the point of contact, rather than sliding toward a valley within a notch of the pull ring 208 to initiate the slit.

Figure 10:
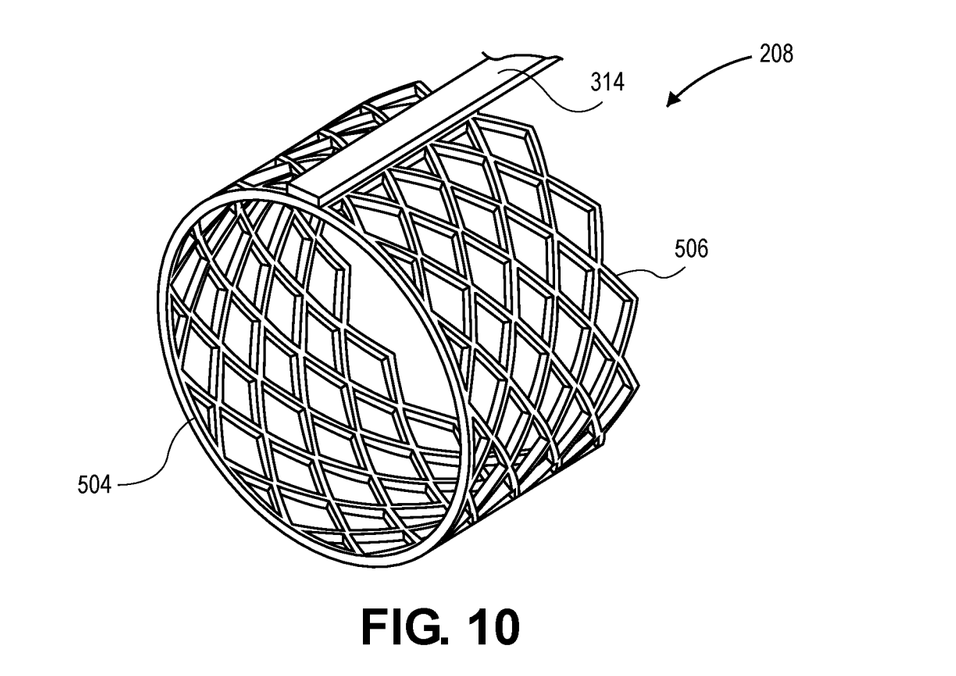

Referring to FIG. 10, a perspective view of a slittable pull ring having a closed distal end is shown in accordance with an embodiment. The illustrated pull ring 208 includes a closed distal end 110, having the closed end structure described with respect to FIG. 9, and an open proximal end 202, having the open end structure described with respect to FIG. 8. By contrast, in an embodiment, the pull ring 208 may include an open distal end and a closed proximal end (not shown).

Figure 11:
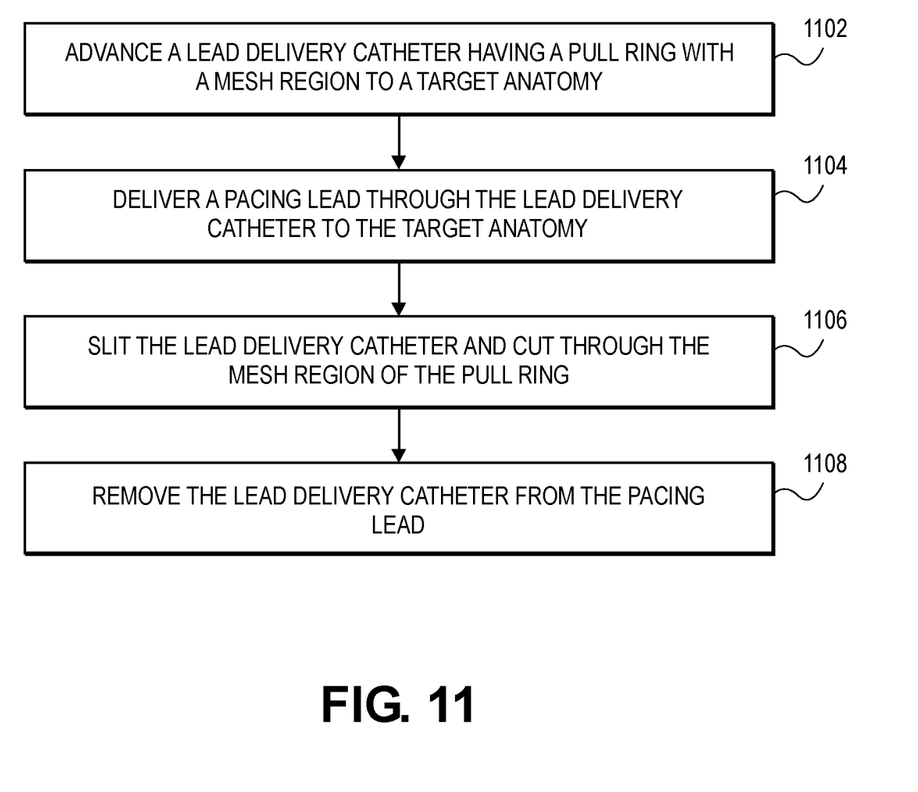
FIG. 11 is a flowchart of a method of delivering a pacing lead to a target anatomy, in accordance with an embodiment.

Referring to FIG. 11, a flowchart of a method of delivering a pacing lead to a target anatomy is shown in accordance with an embodiment. At operation 1102, the lead delivery catheter 100 can be advanced to the target anatomy. The lead delivery catheter 100 can be introduced over a guidewire and tracked through a vasculature of the patient 104 into the chamber of the heart 102. When the distal end 110 of the lead delivery catheter 100 is within the chamber, the physician can manipulate the handle 112 to cause the distal end 110 to steer in a desired direction. For example, the distal end 110 of the catheter shaft 106 can be placed at the bundle of His or another target site. It will be appreciated that the steering capability of the lead delivery catheter 100 can eliminate or reduce the need for fixed curve catheters in the catheterization lab. More particularly, given that the distal end 110 of the catheter shaft 106 can be placed in any location across a travel range of the steering catheter, the physician does not have to use a catheter having a specific curve, or several catheters having specific curves, to reach the target site.

At operation 1104, the physician can deliver the pacing lead through the lead delivery catheter 100 to the target anatomy. A distal tip of the pacing lead can be engaged with the target tissue, e.g., by screwing the distal tip into the tissue. Accordingly, the pacing lead can be implanted in the bundle of His for directly stimulating the specialized ventricular conduction system, or another target site.

After the pacing lead is implanted, the lead delivery catheter 100 can be removed from the patient 104. The physician can disengage the handle 112 from the catheter shaft 106. More particularly, the catheter shaft 106 may include a molded hub at the proximal end 202, which can be detached from the handle 112. The physician can grab the molded hub on the catheter shaft 106 and pull backward on the catheter while advancing a blade of a cutting tool through the catheter shaft wall 404. When the catheter shaft wall 404 is slit, the catheter shaft 106 can be pulled laterally away from the pacing lead without having to retract the proximal end 202 over the electrical connector of the pacing lead.

At operation 1106, the blade of the cutting tool can slit the lead delivery catheter 100 and cut through the pull ring 208. As the blade advances distally through the distal end of the tubular braid 304, the blade can engage the mesh region 609 of the slittable pull ring 208. The slittable pull ring 208 can be any of the pull rings 208 described above, which have material densities and material distribution similar to the tubular braid 304. Accordingly, as the blade advances from the tubular braid 304 into the pull ring 208, the cutting force remains nearly constant. The consistency of the cutting force can reduce or eliminate variations in the forces transmitted from the catheter shaft 106 to the pacing lead. Accordingly, a likelihood that the catheter shaft 106 will jolt or dislodge the pacing lead from the target anatomy may be reduced.

After cutting entirely through the pull ring 208, the blade of the cutting tool can be advanced further to the distal end 110 of the catheter shaft 106. At operation 1108, when the catheter shaft 106 is fully slit, the lead delivery catheter 100 can be removed from the pacing lead. The distal end of the pacing lead can remain intact in the target tissue, and the electrical connector at the proximal end of the pacing lead can be connected to the pacemaker. The physician may then initiate the pacemaker to begin cardiac pacing of the heart 102 by the pacing lead.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A catheter shaft, comprising:
a tubular liner extending along a central axis;
a deflection wire extending along the tubular liner;
a tubular braid extending along the central axis and including a plurality of strands having a strand thickness;
a slittable pull ring mounted on the tubular liner and coupled to the deflection wire distal to the tubular braid, wherein the slittable pull ring includes an annular wall around the central axis, wherein the annular wall includes a mesh region having a lattice formed from columns of ring holes arranged along respective axes extending parallel to the central axis between a proximal edge and a distal edge of the annular wall, wherein adjacent columns of ring holes in the lattice are offset from each other in a circumferential and an axial direction, and wherein adjacent ring holes of the columns of ring holes are separated from each other by an edge-to-edge distance less than twice the strand thickness; and
an external tubular component covering the slittable pull ring such that the lattice is encapsulated between the tubular liner and the external tubular component.

2. The catheter shaft of claim 1, wherein the proximal edge of the annular wall is distal to a distal end of the tubular braid.

3. The catheter shaft of claim 1, wherein the plurality of strands are interlaced around a plurality of braid holes arranged around the central axis such that a braid porosity of the tubular braid is within +/− 20% of a mesh porosity of the mesh region.

4. The catheter shaft of claim 3, wherein a wall thickness of the annular wall is less than or equal to the strand thickness.

5. The catheter shaft of claim 1, wherein the slittable pull ring includes a solid region circumferentially between a first lateral boundary of the mesh region and a second lateral boundary of the mesh region, and wherein the deflection wire is attached to the solid region.

6. The catheter shaft of claim 5, wherein the deflection wire has a wire width, and wherein the solid region has a circumferential width greater than the wire width and less than twice the wire width.

7. The catheter shaft of claim 5 further comprising a second deflection wire extending along the tubular liner, wherein the second deflection wire is attached to the slittable pull ring at a second solid region diametrically opposed to the solid region.

8. A lead delivery catheter, comprising:
a catheter shaft including a tubular liner extending along a central axis, a deflection wire extending along the tubular liner, a tubular braid extending along the central axis and including a plurality of strands having a strand thickness, and a slittable pull ring mounted on the tubular liner and coupled to the deflection wire distal to the tubular braid, wherein the slittable pull ring includes an annular wall around the central axis, wherein the annular wall includes a mesh region having a lattice formed from columns of ring holes arranged along respective axes extending parallel to the central axis between a proximal edge and a distal edge of the annular wall, wherein adjacent columns of ring holes in the lattice are offset from each other in a circumferential and an axial direction, wherein adjacent ring holes of the columns of ring holes are separated from each other by an edge-to-edge distance less than twice the strand thickness, and wherein an external tubular component covers the slittable pull ring such that the lattice is encapsulated between the tubular liner and the external tubular component; and a handle coupled to the catheter shaft to apply tension to the deflection wire to deflect the catheter shaft.

9. The lead delivery catheter of claim 8, wherein the proximal edge of the annular wall is distal to a distal end of the tubular braid.

10. The lead delivery catheter of claim 8, wherein the plurality of strands are interlaced around a plurality of braid holes arranged around the central axis such that a braid porosity of the tubular braid is within +/− 20% of a mesh porosity of the mesh region.

11. The lead delivery catheter of claim 10, wherein a wall thickness of the annular wall is less than or equal to the strand thickness.

12. The lead delivery catheter of claim 8, wherein the slittable pull ring includes a solid region circumferentially between a first lateral boundary of the mesh region and a second lateral boundary of the mesh region, and wherein the deflection wire is attached to the solid region.

13. The lead delivery catheter of claim 12, wherein the deflection wire has a wire width, and wherein the solid region has a circumferential width greater than the wire width and less than twice the wire width.

14. The lead delivery catheter of claim 12 further comprising a second deflection wire extending along the tubular liner, wherein the second deflection wire is attached to the slittable pull ring at a second solid region diametrically opposed to the solid region.

15. A method of delivering a pacing lead to a target anatomy, comprising:

advancing a lead delivery catheter to the target anatomy, wherein the lead delivery catheter includes a catheter shaft including a tubular liner extending along a central axis, a deflection wire extending along the tubular liner, a tubular braid extending along the central axis and including a plurality of strands having a strand thickness, and a slittable pull ring mounted on the tubular liner and coupled to the deflection wire distal to the tubular braid, wherein the slittable pull ring includes an annular wall around the central axis, wherein the annular wall includes a mesh region having a lattice formed from columns of ring holes arranged along respective axes extending parallel to the central axis between a proximal edge and a distal edge of the annular wall, wherein adjacent columns of ring holes in the lattice are offset from each other in a circumferential and an axial direction, wherein adjacent ring holes of the columns of ring holes are separated from each other by an edge-to-edge distance less than twice the strand thickness, and wherein an external tubular component covers the slittable pull ring such that the lattice is encapsulated between the tubular liner and the external tubular component;

delivering the pacing lead through the catheter shaft to the target anatomy;

slitting the lead delivery catheter, wherein the slitting includes cutting through the mesh region of the annular wall and the tubular braid; and removing the lead delivery catheter from the pacing lead.

16. The method of claim 15, wherein the proximal edge of the annular wall is distal to a distal end of the tubular braid.

17. The method of claim 15, wherein the plurality of strands are interlaced around a plurality of braid holes arranged around the central axis such that a braid porosity of the tubular braid is within +/− 20% of a mesh porosity of the mesh region.

18. The method of claim 15, wherein the slittable pull ring includes a solid region circumferentially between a first lateral boundary of the mesh region and a second lateral boundary of the mesh region, and wherein the deflection wire is attached to the solid region.

* * * * *